United States Patent
Lux et al.

(10) Patent No.: US 9,199,889 B2
(45) Date of Patent: Dec. 1, 2015

(54) METHOD AND APPARATUS FOR CONVERSION OF CARBONACEOUS MATERIALS TO LIQUID FUEL

(71) Applicant: Altex Technologies Corporation, Sunnyvale, CA (US)

(72) Inventors: Kenneth W Lux, Newark, CA (US); Mehdi Namazian, Sunnyvale, CA (US); John T Kelly, Saratoga, CA (US)

(73) Assignee: ALTEX TECHNOLOGIES CORPORATION, Sunnyvale, CA (US)

( * ) Notice: Subject to any disclaimer, the term of this patent is extended or adjusted under 35 U.S.C. 154(b) by 0 days.

(21) Appl. No.: 13/815,766

(22) Filed: Mar. 15, 2013

(65) Prior Publication Data
US 2014/0275296 A1 Sep. 18, 2014

(51) Int. Cl.
*C07C 1/10* (2006.01)
*C10G 50/00* (2006.01)
*C10G 57/02* (2006.01)
*C10G 9/36* (2006.01)
*C10L 1/04* (2006.01)

(52) U.S. Cl.
CPC ... *C07C 1/10* (2013.01); *C10G 9/36* (2013.01); *C10G 50/00* (2013.01); *C10G 57/02* (2013.01); *C10L 1/04* (2013.01); *C10G 2400/20* (2013.01)

(58) Field of Classification Search
CPC ...... C07C 1/10; C10G 2400/20; C10G 50/00; C10G 57/02; C10G 9/36; C10L 1/04
USPC ......... 585/240, 324, 329, 648, 650, 801, 502; 518/702
See application file for complete search history.

(56) References Cited

U.S. PATENT DOCUMENTS

| 2,551,579 | A | | 5/1951 | Ernst |
| 4,778,585 | A | | 10/1988 | Graff |
| 4,891,459 | A | * | 1/1990 | Knight et al. ........... 585/240 |
| 5,523,502 | A | | 6/1996 | Rubin |
| 5,639,937 | A | | 6/1997 | Höver et al. |

(Continued)

FOREIGN PATENT DOCUMENTS

| WO | WO 2011053166 | * | 5/2011 |
| WO | WO 2011/156892 A2 | | 12/2011 |

OTHER PUBLICATIONS

Alpha-olefin, from Wikipedia, the free encyclopedia, downloaded from: http://en.wikipedia.org/wiki/Alpha-olefin, Oct. 18, 2013.

(Continued)

*Primary Examiner* — Jafar Parsa
*Assistant Examiner* — Amy C Bonaparte
(74) *Attorney, Agent, or Firm* — Squire Patton Boggs (US) LLP

(57) ABSTRACT

Embodiments of the invention relates to conversion of hydrocarbon material including but not limited to coal and biomass to a synthetic liquid transportation fuel. The invention includes the integration of a non-catalytic first reaction scheme, which converts carbonaceous materials into a solid product that includes char and ash and a gaseous product; a non-catalytic second reaction scheme, which converts a portion of the gaseous product from the first reaction scheme to light olefins and liquid byproducts; a traditional gas-cleanup operations; and the third reaction scheme to combine the olefins from the second reaction scheme to produce a targeted fuel like liquid transportation fuels.

37 Claims, 6 Drawing Sheets

(56) References Cited

U.S. PATENT DOCUMENTS

| | | | |
|---|---|---|---|
| 5,993,751 A * | 11/1999 | Moriarty et al. | 422/233 |
| 7,128,827 B2 | 10/2006 | Tallman et al. | |
| 7,951,289 B2 | 5/2011 | Wu et al. | |
| 7,998,315 B2 | 8/2011 | Bridgwater et al. | |
| 8,183,422 B2 | 5/2012 | Alegria et al. | |
| 2008/0016769 A1 | 1/2008 | Pearson | |
| 2011/0283601 A1* | 11/2011 | Ditsch | 44/307 |
| 2012/0160741 A1 | 6/2012 | Gong et al. | |

OTHER PUBLICATIONS

Cracking (chemistry), from Wikipedia, the free encyclopedia, downloaded from: http://en.wikipedia.org/wiki/Cracking_(chemistry), Oct. 18, 2013.

Fischer-Tropsch process, from Wikipedia, the free encyclopedia, downloaded from: http://en.wikipedia.org/wiki/Fischer%E2%80%93Tropsch_process, Aug. 15, 2012.

Joule-Thomson effect, from Wikipedia, the free encyclopedia, downloaded from: http://en.wikipedia.org/wiki/Joule%E2%80%93Thomson_effect, Oct. 18, 2013.

Pyrolysis, description from Wikipedia, the free encyclopedia, downloaded from: http://wikipedia.org/Pyrolysis, Aug. 15, 2012.

Steam Cracking, Chemistry470—"Industrial Chemistry" Lecture Notes Spring Semester 2012, downloaded from: http://www.chem.tamu.edu/class/majors/chem470/Steam_Cracking.html, Aug. 15, 2012.

International Search Report and Written Opinion in PCT/US2014/025928, mailed Jun. 24, 2014.

Ren et al., Olefins from conventional and heavy feedstocks: Energy use in steam cracking and alternative processes (2006) *Energy* 31:425-451.

* cited by examiner

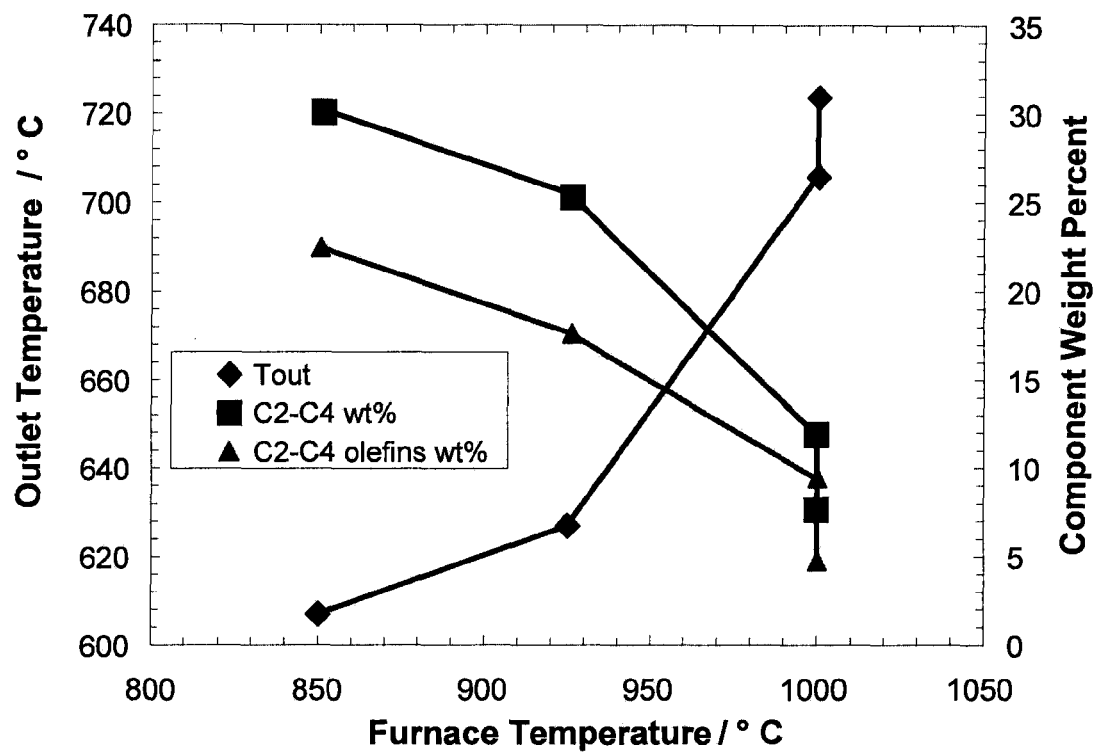
Figure 2. Effect of furnace temperature on outlet temperature and $C_2$-$C_4$ concentrations. Feed: lignite.

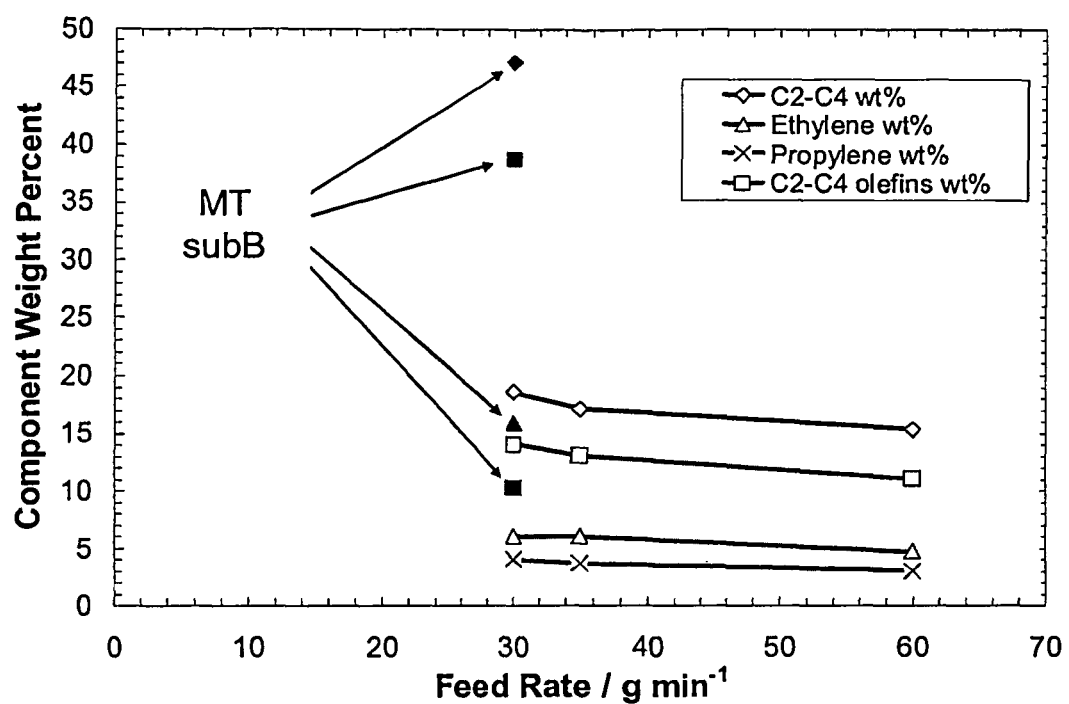
Figure 3. Effect of feed rate on $C_2$-$C_4$ concentrations. Open symbols: lignite, filled symbols: subbituminous coal.

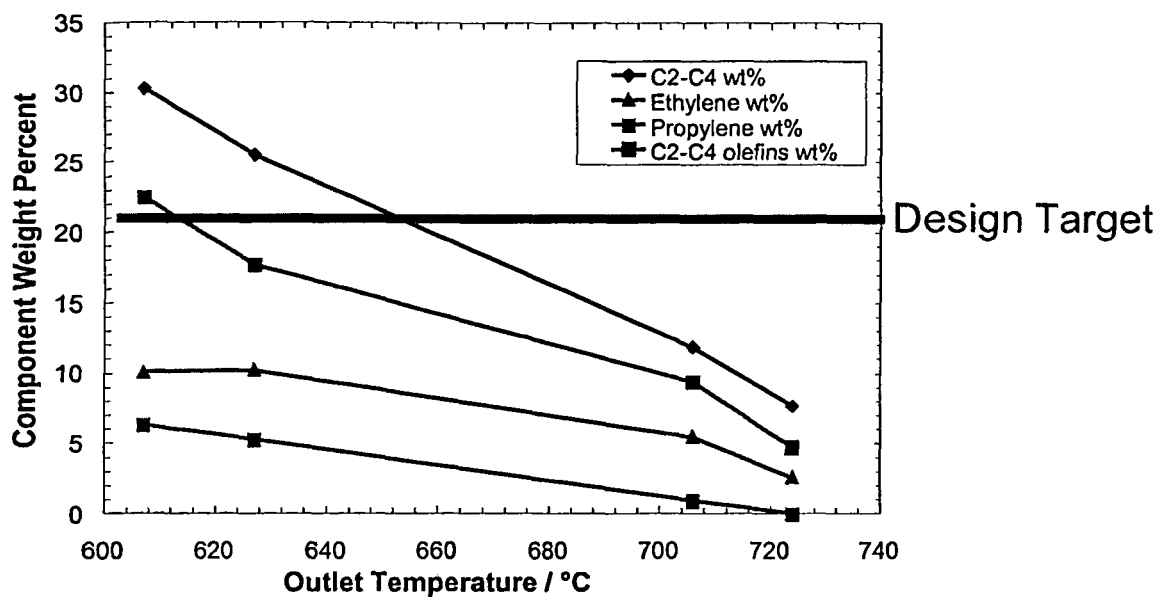
Figure 4. Effect of outlet temperature on $C_2$-$C_4$ yields. Feed: lignite.

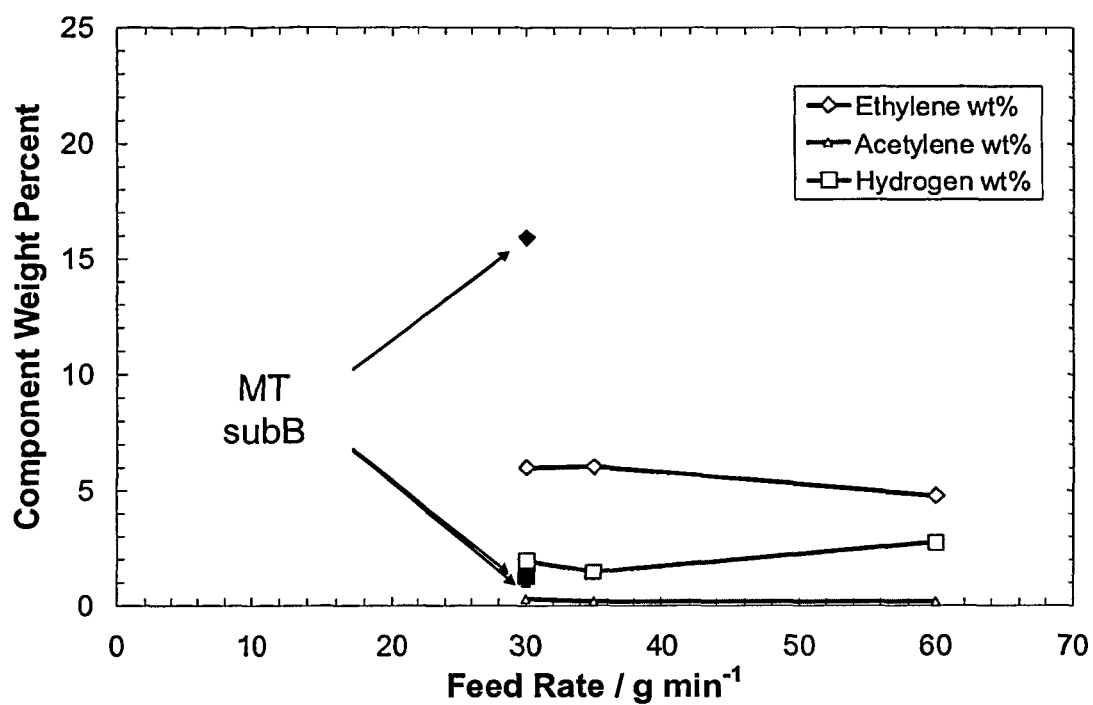
Figure 5. Effect of feed rate on hydrogen, ethylene, and acetylene concentrations. Open symbols: lignite, filled symbols: subbituminous coal.

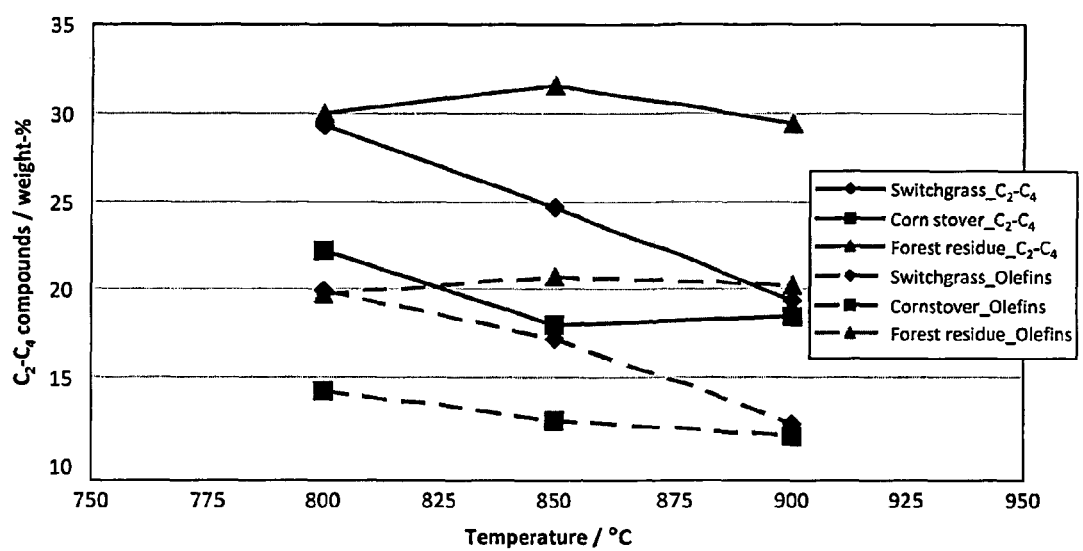
Figure 6. Effect of the temperature of the second reaction scheme on $C_2$-$C_4$ concentrations.

METHOD AND APPARATUS FOR CONVERSION OF CARBONACEOUS MATERIALS TO LIQUID FUEL

STATEMENT OF GOVERNMENT SPONSORED RESEARCH

The embodiments of the invention described herein were reduced to practice with Government support under contract HR0011-09-C-0092 awarded by the Defense Advanced Project Agency (DARPA), contract W911-11-C-0018 awarded by the Army, and contract DE-SC0006466 awarded by the US Department of Energy (DOE). The Government has certain rights in the invention.

FIELD OF THE INVENTION

The present invention relates to conversion of carbonaceous material such as coal and biomass to a synthetic liquid that may be used as a fuel.

BACKGROUND OF THE INVENTION

Conversion of non-petroleum feedstocks into liquid fuels, such as jet fuel, diesel fuel, or gasoline, has long been of interest due to the limited distribution of petroleum reserves and due to the possibility of producing liquid fuels from biomass and/or waste, which can reduce or eliminate life-cycle $CO_2$ emissions for liquid fuels. Current technologies for converting carbonaceous material into liquid fuels tend to fall into two categories: 1) pyrolysis followed by hydrotreating; and 2) gasification followed by Fischer-Tropsch synthesis.

In the first category are processes in which the carbonaceous material is pyrolyzed by heating the feed to temperatures of 500-600° C. in the absence of molecular oxygen. This results in the generation of solid and gaseous products. The solid product, called char and/or ash, is separated from the gaseous products. The gaseous products are cooled to room temperature to condense a portion of the gaseous products into a liquid that superficially resembles crude oil called pyrolysis oil, or when the carbonaceous material is biomass, bio-oil. The pyrolysis-oil is then further processed to produce a liquid fuel.

However, when the carbonaceous material contains oxygen—as is the case for materials such as coal, biomass, municipal solid waste, etc.—a significant amount of oxygen is incorporated into the molecules of which the pyrolysis oil is comprised. The oxygen in the pyrolysis oil is often manifested in functional groups such as hydroxyl and carboxylic-acid groups. The presence of these compounds in the pyrolysis oil results in a pyrolysis oil that has a low heating value, a very high acidity, and lacks stability. The low heating value reduces the value of the pyrolysis oil as a fuel or feedstock for producing fuel, the high acidity makes it incompatible with the existing petroleum infrastructure, and the instability results in excessive gum formation and increases in viscosity when stored at or above room temperature.

In order to address these issues with pyrolysis oil, it is often hydrotreated with hydrogen to remove the oxygen. This results in a pyrolysis oil that has acceptable properties at mass yields of up to 30% depending upon the feedstock and if the source of hydrogen is natural gas. However, the production of hydrogen requires additional equipment operating at high temperatures and pressures and, in some cases, a source of water. These requirements increase the cost of producing a marketable product. Also, depending upon the source of the fuel used to produce the hydrogen, there may be an increase in fossil-fuel-derived $CO_2$ emissions or a reduction in yield.

In the second category are processes where the carbonaceous material is gasified at temperatures of 800-1000° C. to produce synthesis gas (mainly CO and $H_2$). Because gasification yields a composition close to equilibrium, the specific chemical makeup of the feed only affects the H:C and C:O ratios in the synthesis gas, thus making control of the composition of the final product straightforward. After removing contaminants from the hot gas, a Fischer-Tropsch (F-T) process is employed to link $C_1$ compounds (e.g., CO, $CH_4$, etc.) to produce a targeted hydrocarbon product such as synthetic JP-8 jet fuel. This makes a synthetic fuel that is very close to the desired product. However, this approach is very expensive due, in part, to both the catalytic F-T process, but also due to the complexities of hot-gas clean-up.

There is a continuing need for technologies that convert carbonaceous material to a synthetic fuel at a cost competitive with traditional petroleum-derived fuels.

SUMMARY OF THE INVENTION

In response to this need, novel processes are described that obviate the limitations and disadvantages of the current processes described above and converts carbonaceous material into intermediate gases that are used as building blocks for producing a liquid that may be used as a targeted fuel (e.g., jet fuel, gasoline). In some embodiments of the invention, the carbonaceous materials—such as coal, biomass, or waste—is fed to a first reaction scheme wherein the feed heated in the absence of molecular oxygen to produce a solid containing char and ash and volatile gases. In contrast to the prior art wherein the volatile gases are partially condensed to form pyrolysis oil, the volatile gases are fed directly to a second reaction scheme wherein a non-catalytic reactor converts a portion of the volatile gases into a mixture of light olefins, predominantly ethylene and propylene. This process, like gasification in the gasification/F-T processes, effectively normalizes the volatile gas feed by converting it into a gas stream that is relatively independent of the feed composition. In further embodiments, in a fashion similar to the linking of $C_1$ compounds in F-T synthesis, the stream containing light olefins, which are reactive towards oligomerization using very inexpensive catalysts, are optionally first cleaned using standard gas-cleanup techniques and then fed to a third reaction scheme where they are linked together to produce hydrocarbons of the correct molecular weight for the targeted synthetic fuel. This use of light olefins as building blocks results in good control of the product composition as with a traditional gasification/F-T process. However, it also reduces cost by avoiding the need for hot-gas cleanup and F-T catalysts. In contrast to traditional pyrolysis, the main product can be used as a high-value liquid fuel. By combining inexpensive feedstock and the best aspects of pyrolysis processes (e.g., lower cost) and gasification/F-T processes (e.g., finer product control) with oligomerization of the light olefins produced, the process embodiments of the invention enable the production of synthetic fuel from carbonaceous material at a relatively low cost.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent there are any inconsistent usages of words and/or phrases between an incorporated publication, patent, or patent application and the present specification, these words and/or phrases will have a meaning that is consistent with the manner in which they are used in the present specification.

BRIEF DESCRIPTION OF THE DRAWINGS

FIG. 2: For an embodiment of the present invention, the effect of furnace temperature on outlet temperature and $C_2$-$C_4$ concentrations. Feed: lignite.

FIG. 3: For an embodiment of the present invention, the effect of feed rate on $C_2$-$C_4$ concentrations. Open symbols: lignite, filled symbols: subbituminous coal.

FIG. 4: For an embodiment of the present invention, the effect of outlet temperature on $C_2$-$C_4$ yields. Feed: lignite.

FIG. 5: For an embodiment of the present invention, the effect of feed rate on hydrogen, ethylene, and acetylene concentrations. Open symbols: lignite, filled symbols: subbituminous coal.

FIG. 6: For an embodiment of the present invention, the effect of the temperature of the second reaction scheme on $C_2$-$C_4$ concentrations. Feed: ligno-cellulosic biomass.

DETAILED DESCRIPTION OF EMBODIMENTS

Figure 1:
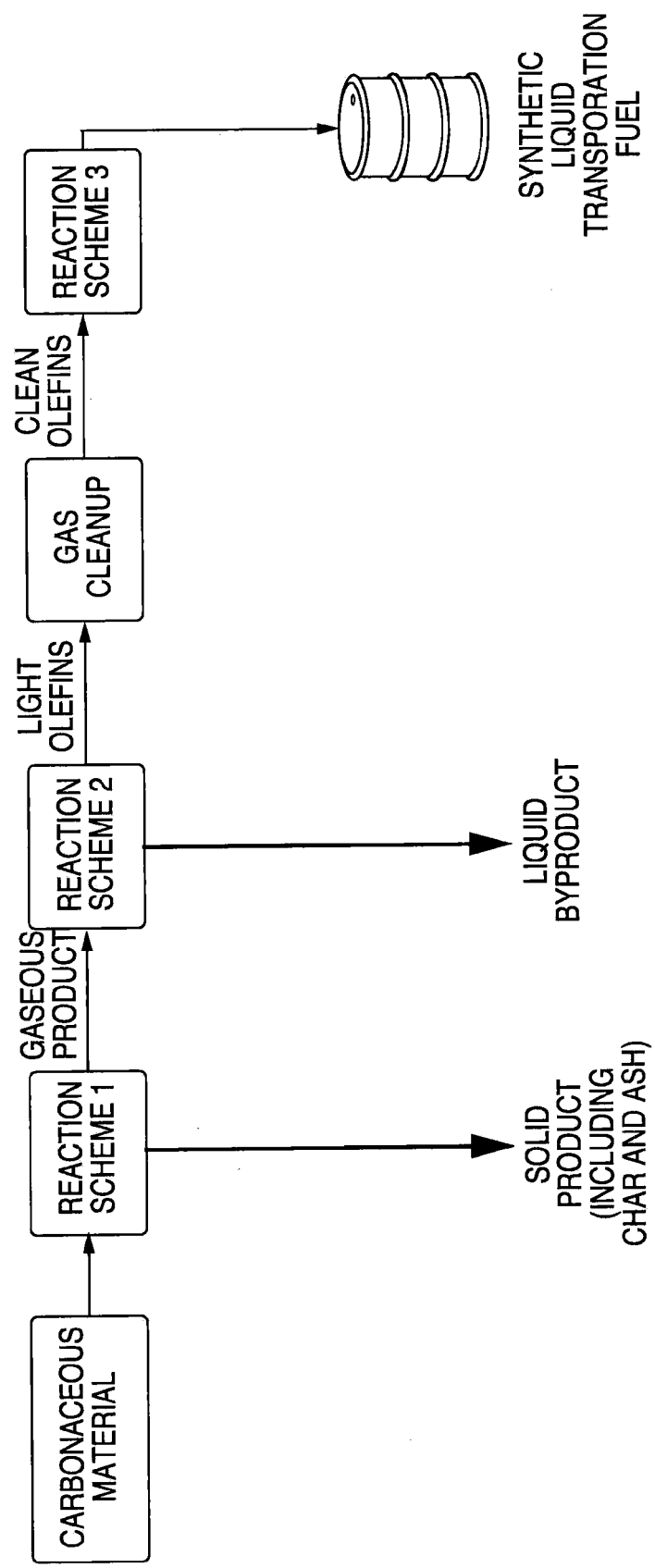
FIG. 1: Broad process diagram of an embodiment of the invention.

Use of the singular herein, including the claims, includes the plural and vice versa unless expressly stated to be otherwise. That is, "a" and "the" refer to one or more of whatever the word modifies. For example, "a product" may refer to one product, two products, etc. Likewise, "the reaction" may mean one reaction or a plurality of reactions. By the same token, words such as, without limitation, "products" and "reactions" would refer to one product or reaction as well as to a plurality of products or reactions unless it is expressly stated or obvious from the context that such is not intended.

As used herein, unless specified otherwise, any words of approximation such as without limitation, "about," "essentially," "substantially" and the like mean that the element so modified need not be exactly what is described but can vary from the description by as much as ±15% without exceeding the scope of this invention.

As used herein, any ranges presented are inclusive of the end-points. For example, "a temperature between 500° C. and 600° C." or "a temperature from 500° C. to 600° C." includes 500° C. and 600° C., as well as any temperature in between.

As used herein, the use of "preferred," "preferably," "more preferred," and the like to modify an aspect of the invention refers to preferences as they existed at the time of filing of the patent application.

As used herein, including the claims, the phrase "deg C." refers to degrees Celsius.

As used herein, including the claims, "molecular oxygen" refers to the chemical compound comprised of two oxygen atoms (i.e., with chemical formula $O_2$)

As used herein, including the claims, "atm" refers to atmospheres.

As used herein, including the claims, "sec" refers to second or seconds.

As used herein, including the claims, "e.g." is used to introduce a non-exclusive list of example items and is not intended, as used herein, including the claims, to list all possible items.

As used herein, including the claims, "wt %" refers to "weight percent."

Embodiments of the present invention encompass the integration of two reaction schemes to convert carbonaceous material into a solid product of char and ash, a gaseous product containing light olefins, and liquid byproducts. Optionally, a third reaction scheme may be integrated. Thus, some embodiments include the further integration of a third reaction scheme to produce a liquid product, such as a targeted liquid fuel, from the olefins.

An embodiment of the invention is shown in FIG. 1. The carbonaceous feedstock (e.g., coal, biomass, waste) is converted with a first reaction scheme to a gaseous component including condensable gases which includes hydrocarbons and a solid component including char and ash. The gaseous component is fed to a second reaction scheme where the condensable gases and the non-condensable gases that contain 2 or more carbon atoms are converted to reaction products including light olefins. Optionally, a portion of the reaction products of the second reaction scheme may be converted with a third reaction scheme to a liquid product, such as a product that is substantially a targeted liquid fuel.

A carbonaceous material is any material including carbon and hydrogen. It may include other elements such as without limitation oxygen, nitrogen, sulfur, etc. Non-limiting examples include coal, biomass, paper, cardboard, wood, wheat straw, switchgrass, and waste. In some embodiments, the carbonaceous material serving as the input to the first reaction scheme is a combination of different types of carbonaceous materials.

A liquid fuel is a liquid product that complies with the specifications for a targeted fuel, or a liquid product that may be used as a fuel. Non-limiting examples include gasoline, jet fuel (JP-5, JP-8), and diesel.

Condensable gases are those substances that exist as a liquid at 25 deg C. and 1 atm pressure.

Non-condensable gases are those substances that do not exist as a liquid at 25 deg C. and 1 atm pressure.

The first reaction scheme may incorporate a non-catalytic reactor similar to a fast-pyrolysis reactor. In fast-pyrolysis reactors, a carbonaceous feedstock is heated in the absence of molecular oxygen to a high temperature, such as but not limited to, around 600 deg C., in a short time period, such as but not limited to, less than 1 second, and optionally, also not less than 0.0001 sec. This converts the carbonaceous feedstock to a solid product containing char and ash and a gaseous product containing condensable gases and non-condensable gases. The gaseous component can be cooled to produce an oil-like liquid from the condensable hydrocarbons in the gaseous product called pyrolysis oil. In conventional processes, the gaseous component is cooled to produce pyrolysis oil.

In some embodiments, the first reaction scheme is terminated prior to equilibrium to obtain the composition of condensable gases, non-condensable gases that contain 2 or more carbon atoms, or both.

In the embodiments of the present invention, the gaseous product is not cooled to produce pyrolysis oil. The gaseous product instead is fed directly to the second reaction scheme.

The second reaction scheme may incorporate a non-catalytic reactor that is similar to the radiant section of a steam cracker. As used extensively in the ethylene industry, a steam cracker is fed a hydrocarbon gas (e.g., ethane) or hydrocarbon liquid (e.g., naphtha) and water. The convective section of a furnace preheats the feed and water to produce a gaseous feed to the radiant section of the furnace. Rapidly heating this mixture in the radiant section of the furnace to high temperatures, above around 600° C. (such as 600-1000 deg C., preferably 700-1000 deg C., and more preferably 800-1000 deg C.), and rapidly cooling the reaction products after a short residence time (e.g. <5 sec, preferably <1 sec, and more preferably <0.1 sec, and optionally, not less than 0.000001 sec) results in the hydrocarbon gas or hydrocarbon liquid being converted to light olefins (e.g., $C_2$-$C_4$ olefins where the subscript after the "C" represents the number of carbons in the compound) as well as other byproducts including hydrogen, light alkanes, light alkynes, and aromatic compounds. A rapid cooling of the product gas freezes out polymerization reactions and minimizes the production of higher molecular-weight compounds. The high-molecular-weight byproducts that are formed are easily separated from the light olefins and recovered as pyrolysis oil and pyrolysis gasoline.

In the embodiments of the invention, the reactor in the second reaction scheme would be similar only to the radiant section of a steam cracker and not include the convective section of a conventional steam cracker.

It is important to note that, to date, steam crackers have operated on gas and liquid feeds that contain negligible amounts of oxygen. They are specifically intended for and designed for production of ethylene and propylene from oxygen-free gas and oxygen-free liquid feeds. Using a steam cracker for the processing of feeds containing oxygen, particularly a solid feed containing oxygen, is not a conventional use. The embodiments of the present invention utilize conditions similar to those utilized in the radiant section of a traditional steam cracker to convert oxygenated feeds into light olefins. Importantly, this reaction scheme not only serves to produce light olefins, but also serves to convert oxygen-containing functional groups to CO and $CO_2$. Therefore, this reaction scheme also utilizes a reactor similar to a traditional steam cracker as a means of not only producing light olefins, but also for simultaneously converting the oxygen in oxygenated feedstocks and excess carbon into a form that can be readily separated from the light olefins or that does not participate in the reactions used to produce the liquid-fuel product. This is an additional advantage of the embodiments of the present invention.

In some embodiments, the first reaction scheme increases the H:C ratio of the input, by at least 5%, preferably at least 10%, and more preferably at least 20%, and the second reaction scheme decreases the O:C ratio of the input by at least 5%, preferably 10%, and more preferably 20%. In this manner, the embodiments of the invention increase the H:C ratio and reduce the O:C ratio without requiring the addition of hydrogen.

In some embodiments, the first and second reaction scheme are executed in separate pieces of equipment, and in other embodiments, the first and second reaction scheme are executed in one piece of equipment.

Optionally, at least a portion of the olefins, and optionally a portion of the gaseous byproducts from the second reaction scheme, are fed to a third reaction scheme. In some embodiments, light byproducts that may interfere with downstream reactions (e.g., $H_2S$, COS, $NH_3$). Thus in some embodiments, the light olefins and gaseous byproducts may be fed to traditional gas cleanup operations using traditional gas cleanup techniques. For example, the acid-gas components (e.g., $CO_2$, COS, and $H_2S$) and $NH_3$ may be removed with an amine loop. In some embodiments, optionally after removal of acid-gas components and $NH_3$, other non-condensable byproducts (e.g., CO, $H_2$, $CH_4$) are removed through a simple Joule-Thomson cryogenic cycle before the light-olefin stream is fed to the third reaction scheme, which may be an oligomerization reactor. Other gas clean-up techniques that are known in the art may be used. In some embodiments, there are no gas clean-up processes before at least a portion of the reaction products of the second reaction scheme are fed to the third reaction scheme. In some embodiments, compounds which are not olefins (e.g., CO, $H_2$, $CH_4$) pass through the third reaction scheme unchanged, or substantially unchanged.

The third reaction scheme may incorporate a catalytic reactor similar to a traditional oligomerization reactor. The production of liquids from oligomerization of light olefins is known to practitioners of the art. However, conventionally, this approach has been limited to processes utilizing light olefins derived from petroleum refining as the feedstock. As such, the feeds to traditional oligomerization reactors contain no oxygen, either as molecular oxygen or as oxygen atoms combined with carbon atoms (e.g. CO).

In some embodiments of the invention, the feed to the third reaction scheme may include oxygenated compounds (e.g. CO) or other compounds not generated in petroleum-refinery operations. The presence of these compounds may impact oligomerization-reactor performance and design as well as the choice of catalyst for use in the oligomerization reactor. Therefore, the integration of the third reaction scheme with the first and second reactions schemes involves more than the addition of a process using a conventional reactor operating at conventional reactor conditions to the end of the equipment train.

The third reaction scheme is selected based upon the choice of targeted liquid fuel. The reaction pressure, temperature, and space velocity, as well as the choice of catalyst will depend upon the targeted liquid fuel, and may be impacted by the choice of carbonaceous feed to the first reaction scheme. However, it is believed that the specifics of the third reaction scheme are relatively insensitive to the choice of carbonaceous feed to the first reaction scheme. The third reaction scheme is essentially an oligomerization reaction, and one of skill in the art would know be able to select the oligomerization reaction scheme based on what is known to one of skill in the art and the disclosure herein.

In some embodiments of the invention, the third reaction scheme utilizes an oligomerization reactor wherein the light olefins are oligomerized to form linear α-olefins with a carbon-number distribution that matches that of the targeted fuel. It should be noted that in the oligomerization reactor the linear α-olefins formed from oligomerization of the light olefins are further converted into cycloparaffins to stabilize the liquid fuel and match the key specifications for the fuel properties of interest.

In some embodiments, the liquid product that may be used as a fuel produced from the integration of the first, second, and third reaction schemes, is jet fuel including, but not limited to, JP-5 and JP-8. In some embodiments, the liquid fuel produced from the integration of the first, second, and third reaction schemes, is gasoline, and in still other embodiments the liquid fuel produced is diesel. In some embodiments, the liquid product of the integration of the first, second, and third reaction schemes, is at least 60 wt %, at least 65 wt %, or at least 70 wt % a liquid that may be used as a fuel, such as a targeted liquid fuel.

Example 1

Laboratory Tests of the Process with Lignite and Subbituminous Coal

One type of carbonaceous material that can be utilized as the feedstock for process embodiments of the invention is coal. Coal refers to a broad range of materials classified by rank, which is, in general, an indication of the geological age of the material. Of particular interest is the use of low-rank coal such as lignite and sub-bituminous coal. Importantly, these materials contain a considerable amount of oxygen. This oxygen can be in the form of water or it can be incorporated into the chemical structure of the coal.

An experimental apparatus that integrated first and second reaction schemes, in this example a pyrolyzer and a cracking furnace, was used to test an embodiment of the invention with lignite and subbituminous coal. The first two reaction schemes were integrated as this arrangement avoids condensation and re-vaporization of the condensable gases, from the first reaction scheme. The pyrolyzer was operated in such a manner that the feed was heated to a reaction temperature of 350-550° C. in 1-10 sec. Higher heating rates would produce higher yields of condensable gases, and hence better overall yield. Operating at moderate heating rates enabled testing the first two reaction schemes under conditions that would yield conservative results for yields. Lignite and sub-bituminous coal were fed to this apparatus. The results of these tests are presented in FIG. 2 through FIG. 5.

FIG. 2 shows the effect of the temperature of the furnace used to provide the heat required by the second reaction scheme on the outlet temperature of this reaction scheme (i.e., the temperature of the reaction products). This test was carried out with lignite as the feed. Higher furnace temperatures lead to higher outlet temperatures and lower $C_2$-$C_4$ concentrations as more $H_2$ and $CH_4$ are produced at higher temperatures.

FIG. 3 shows the effect of feed rate on the $C_2$-$C_4$ concentrations. Data for lignite are shown as open symbols. Data for subbituminous coal are shown as filled symbols. The data for lignite show that higher feed rates lead to slightly lower concentrations. The data for subbituminous coal shows higher yields than for lignite, consistent with the higher hydrocarbon yield from pyrolysis of subbituminous coal as compared to lignite as reported in the literature.

FIG. 4 shows the concentrations of $C_2$-$C_4$ compounds as a function of outlet temperature for lignite. Consistent with the data shown in FIG. 2, the concentrations of $C_2$-$C_4$ compounds decrease with increasing outlet temperature. Also shown in FIG. 4 is the design target for the concentration of $C_2$-$C_4$ compounds as determined by process-flow simulations of a complete liquid-fuel-production plant using a process embodiment of the present invention.

FIG. 5 shows the concentrations of hydrogen, ethylene, and acetylene as a function of feed rate for lignite (open symbols) and the concentrations of hydrogen, ethylene, and acetylene for subbituminous coal at one particular feed rate. At higher feed rates, the concentration of ethylene decreases while the concentration of hydrogen increases.

The data shown in FIG. 2 through FIG. 5 demonstrate that the first two reaction schemes can be combined to produce light olefins that can be utilized by the third reaction scheme to produce a liquid fuel.

To test the conversion of the light-olefin-containing stream from the second reaction scheme to JP-8, a liquid fuel, tests were conducted with bottled gas representing a typical gas composition of the light-olefin-containing stream after gas clean up. The tests were performed using a proprietary catalyst developed by and available for license from Pennsylvania State University. The best operating conditions and the effect of impurities, such as $H_2S$, on the process were also determined.

In this test of one of the embodiments of the invention, the process was able to produce a liquid hydrocarbon fuel with a boiling point less than 320° C. with a yield of more than 80%. The results demonstrated that the test product of the third reaction scheme is similar to JP-8. This is borne out by a comparison of the properties of the synthetic JP-8 (test product) to a typical sample of JP-8 as shown in Table 1. It can be seen that an embodiment of the invention is able to produce a synthetic JP-8 from coal, a carbonaceous material.

TABLE 1

Properties of the Test Product and JP-8.

| Fuel | Product | JP-8 |
|---|---|---|
| Density (g/mL) | 0.8052 (25° C.) | 0.77-0.84 |
| D2887 Distillation | | |
| 10% Recovered | 135° C. | <186° C. |
| Final Boiling Point | 290° C. | <330° C. |
| Cloud point (° C.) | −44.5 | −47 |
| Carbon content (wt %) | 85.8 | — |
| Hydrogen content (wt %) | 13.4 | >13.4 |
| Sulfur (ppm) | 2.3 | 1000 |
| Olefins (%) | <1% | 0.5 |
| Aromatic compounds (%) | 22% | <25% |

Example 2

Laboratory Tests of the Process with Ligno-Cellulosic Biomass

The production of gasoline from ligno-cellulosic biomass was tested using a proprietary catalyst developed by and available for license from Pennsylvania State University. The results demonstrated that production of olefins from lingocellulosic biomass is feasible and that a liquid product similar to gasoline can be obtained through oligomerization. FIG. 6 illustrates that the variation in the $C_2$-$C_4$ compounds with the temperature of the second reaction scheme and for various carbonaceous starting materials. Increasing the reaction temperature of the second reaction scheme generally results in a reduction in the $C_2$-$C_4$ compounds, which is consistent with the results in Example 1 (c.f. FIG. 3 and FIG. 4). It should be noted that by changing the catalyst or reactor operating pressure or reactor operating temperature, liquids with different molecular weights can be produced making the process extremely flexible and able to create jet fuel (eg. JP-8 and JP-5) or gasoline.

Economic Feasibility

In order to construct a full-scale plant, both the feasibility and scalability of the process needs to be shown. Laboratory tests have shown embodiments of the invention are technically feasible based on laboratory-scale tests and analyses.

A Class 4 economic analysis of the process of an embodiment of the invention at a scale of 100,000 BPSD was conducted. A similar analysis of the process converting lingocellulosic biomass to gasoline was also conducted for a smaller scale plant for a similar embodiment of the invention. The results of these analyses were compared to the DOE design cases for several CTL (Coal To Liquid), BTL (Biomass to Liquid), and CBTL (Coal and Biomass to Liquid) processes. While the economic assumptions vary from case to case, the process economics data of the embodiment of the invention compares rather favorably to the DOE design cases when similar economic variable are included. The capital cost for an embodiment of the invention is less than DOE design cases. Including operating and financing costs result in embodiments of the invention producing fuel at a lower price than the DOE design cases.

Some non-limiting embodiments of the present invention are described in the following numbered paragraphs:

[1] Embodiments include a process comprising: executing an operation comprising converting a carbonaceous material with a first reaction scheme to products comprising a gaseous component comprising condensable gases and a solid component comprising char and ash, wherein a temperature of the first reaction scheme reaches 350 to 600 deg C.; and executing an operation comprising converting at least a portion of the condensable gases and at least a portion of the non-condensable gases that contain two or more carbon atoms with a second reaction scheme to reaction products comprising olefins, wherein a temperature of second reaction scheme reaches 600 to 1000 deg C. and a residence time of the second reaction scheme is less than 5 sec. Other embodiments include a process comprising: converting a carbonaceous material with a first reaction scheme to products comprising a gaseous component comprising condensable gases and a solid component comprising char and ash, wherein a temperature of the first reaction scheme reaches 350 to 600 deg C.; and converting at least a portion of the condensable gases and at least a portion of the non-condensable gases that contain two or more carbon atoms with a second reaction scheme to reaction products comprising olefins, wherein a temperature of second reaction scheme reaches 600 to 1000 deg C. and a residence time of the second reaction scheme is less than 5 sec.

[2] In some embodiments, such as described in paragraph [1], a residence time of the first reaction scheme is less than 5 sec.

[3] In some embodiments, such as described in paragraph [2], the residence time of the first reaction scheme is less than 2.5 sec.

[4] In some embodiments, such as described in paragraph [3], the residence time of the first reaction scheme is less than 1 sec.

[5] In some embodiments, such as any of those described in paragraphs [1]-[4], the residence time of the first reaction scheme is not less than $1 \times 10^{-9}$ sec.

[6] In some embodiments, such as any of those described in paragraphs [1]-[5], the residence time of the second reaction scheme is less than 1 sec.

[7] In some embodiments, such as described in paragraph [6], the residence time of the second reaction scheme is less than 0.1 sec.

[8] In some embodiments, such as any of those described in paragraphs [1]-[7], the residence time of the second reaction scheme is not less than $1 \times 10^{-9}$ sec.

[9] In some embodiments, such as any of those described in paragraphs [1]-[8], the temperature of the second reaction scheme is 700 to 1000 deg C.

[10] In some embodiments, such as described in paragraph [9], the temperature of the second reaction scheme is 800 to 1000 deg C.

[11] In some embodiments, such as described in paragraph [10], the temperature of the second reaction scheme is 800 to 900 deg C.

[12] In some embodiments, such as any of those described in paragraphs [1]-[11], the temperature of the first reaction scheme is 450 to 600 deg C.

[13] In some embodiments, such as described in paragraph [12], the temperature of the first reaction scheme is 500 to 600 deg C.

[14] In some embodiments, such as any of those described in paragraphs [1]-[13], the carbonaceous material is solid.

[15] In some embodiments, such as any of those described in paragraphs [1]-[14], steam is an input to the first reaction scheme.

[16] In some embodiments, such as any of those described in paragraphs [1]-[15], the first reaction scheme is pyrolysis performed in the absence of a catalyst.

[17] In some embodiments, such as any of those described in paragraphs [1]-[16], the first reaction scheme, the second reaction scheme, or both are terminated prior to equilibrium.

[18] In some embodiments, such as any of those described in paragraphs [1]-[17], further comprising separating the solid component from the condensable gases.

[19] In some embodiments, such as any of those described in paragraphs [1]-[18], the condensable gases are at least 1 wt % of the gaseous component on a dry basis, and not more than 99.9 wt %.

[20] In some embodiments, such as described in paragraph [19], the condensable gases are at least 5 wt % of the gaseous component on a dry basis.

[21] In some embodiments, such as described in paragraph [20], the condensable gases are at least 10 wt % of the gaseous component on a dry basis.

[22] In some embodiments, such as any of those described in paragraphs [1]-[21], the non-condensable gases are not more than 99 wt % of the gaseous component on a dry basis, and not less than 0.000001 wt %, subject to the proviso that the total of the non-condensable and condensable gases is equal to or less than 100 wt %.

[23] In some embodiments, such as described in paragraph [22], the non-condensable gases are not more than 95 wt % of the gaseous component on a dry basis.

[24] In some embodiments, such as described in paragraph [23], the non-condensable gases are not more than 90 wt % of the gaseous component on a dry basis.

[25] In some embodiments, such as any of those described in paragraphs [1]-[24], the wherein an H:C ratio of the hydrocarbon portion of the condensable gases is 0.8 to 4.

[26] In some embodiments, such as described in paragraph [25], the H:C ratio of the hydrocarbon portion of the condensable gaseous component is 1 to 3.

[27] In some embodiments, such as described in paragraph [26], the H:C ratio of the hydrocarbon portion of the condensable gaseous component is 1.6 to 2.

[28] In some embodiments, such as any of those described in paragraphs [1]-[27], the second reaction scheme is performed in the presence of steam and in the absence of molecular oxygen.

[29] In some embodiments, such as any of those described in paragraphs [1]-[28], the condensable gases comprise substances that are a liquid at 25 deg C. and 1 atm pressure.

[30] In some embodiments, such as any of those described in paragraphs [1]-[29], the condensable gases and the non-condensable gases that that contain two or more carbon atoms that form the feed to the second reaction scheme comprise at least 0.5 wt % oxygen on a dry basis, and not more than 95 wt %.

[31] In some embodiments, such as described in paragraph [30], the condensable gases and the non-condensable gases that contain two or more carbon atoms that form the feed to the second reaction scheme comprise at least 1 wt % oxygen on a dry basis.

[32] In some embodiments, such as described in paragraph [31], the condensable gases and the non-condensable gases that contain two or more carbon atoms that form the feed to the second reaction scheme comprise at least 5 wt % oxygen on a dry basis, but not more than 90 wt %.

[33] In some embodiments, such as any of those described in paragraphs [1]-[32], wherein at least 30 wt % and not more than 99.9 wt % of the olefins are of 2 to 4 carbons.

[34] In some embodiments, such as any of those described in paragraphs [1]-[33], further comprising executing an operation comprising converting at least a portion of the reaction products from the second reaction scheme to a liquid product with a third reaction scheme wherein the liquid product is at least 60% by weight a liquid fuel. In other embodiments, such as any of those described in paragraphs [1]-[33], further comprising converting at least a portion of the reaction products from the second reaction scheme to a liquid product with a third reaction scheme wherein the liquid product is at least 60% by weight a liquid fuel.

[35] In some embodiments, such as described in paragraph [34], the liquid product is at least 65% by weight a liquid fuel.

[36] In some embodiments, such as described in paragraph [35], the liquid product is at least 70% by weight a liquid fuel.

[37] In some embodiments, such as any of those described in paragraphs [34]-[36], the third reaction scheme is performed in the presence of a catalyst.

[38] In some embodiments, such as any of those described in paragraphs [34]-[37], the third reaction scheme is oligomerization.

[39] In some embodiments, such as any of those described in paragraphs [34]-[38], the portion of the reaction products from the second reaction scheme that are fed to the third reaction scheme comprise at least 0.1 wt % oxygen on a dry basis, and not more than 95 wt %.

[40] In some embodiments, such as described in paragraph [39], the portion of the reaction products from the second reaction scheme that are fed to the third reaction scheme comprise at least 1 wt % oxygen on a dry basis.

[41] In some embodiments, such as described in paragraph [40], the portion of the reaction products from the second reaction scheme that are fed to the third reaction scheme comprise at least 5 wt % oxygen on a dry basis.

[42] In some embodiments, such as any of those described in paragraphs [34]-[41], further comprising cleaning the gaseous reaction products of the second reaction scheme to remove species that poison catalysts prior to feeding the gaseous reaction products to the third reaction scheme.

[43] In some embodiments, a process comprising: converting a carbonaceous material with a first reaction scheme to reaction products comprising a gaseous component and a solid component, wherein the temperature and residence time of the first reaction scheme are selected to maximize a composition of condensable gases that are hydrocarbons in the gaseous component and char and ash in the solid component; and converting at least a portion of the condensable gases and optionally at least a portion of the non-condensable gases that contain 2 or more carbon atoms with a second reaction scheme to reaction products including gaseous hydrocarbons, wherein the temperature and residence time of the second reaction scheme are controlled to maximize the composition of the gaseous hydrocarbons to be olefins.

[44] In some embodiments, such as described in paragraph [43], the temperature and residence time of the second reaction scheme are controlled to maximize the composition of the gaseous hydrocarbons to be olefins with carbon numbers between 2 and 4.

[45] In some embodiments, such as described in paragraph [43] or [44], further comprising separating the condensable hydrocarbons from the solid component.

[46] In some embodiments, such as described in any of paragraphs [43]-[45], the carbonaceous material is solid.

[47] In some embodiments, such as any of those described in paragraphs [43]-[46], an H:C of the gaseous hydrocarbons is 0.8 to 4.

[48] In some embodiments, such as described in paragraph [47], an H:C ratio of the gaseous hydrocarbons is 1 to 3.

[49] In some embodiments, such as described in paragraph [48], an H:C ratio of the gaseous hydrocarbons is 1.6 to 2.

[50] In some embodiments, such as any of those described in paragraphs [43]-[49], the first reaction scheme is pyrolysis performed in the absence of a catalyst.

[51] In some embodiments, such as any of those described in paragraphs [43]-[50], the temperature of first reaction scheme reaches 350 to 600 deg C., and the residence time of the first reaction scheme being less than 5 sec.

[52] In some embodiments, such as described in paragraph [51], the temperature of first reaction scheme reaches 350 to 600 deg C., and the residence time of the first reaction scheme being less than 2.5 sec.

[53] In some embodiments, such as described in paragraph [52], the temperature of first reaction scheme reaches 350 to 600 deg C., and wherein the residence time of the first reaction scheme being less than 1 sec.

[54] In some embodiments, such as any of those described in paragraphs [43]-[53], the temperature of second reaction scheme reaches 600 to 1000 deg C. with the residence time of the second reaction scheme being less than 5 sec.

[55] In some embodiments, such as described in paragraph [54], the temperature of second reaction scheme reaches 600 to 1000 deg C. with the residence time of the second reaction scheme being less than 1 sec.

[56] In some embodiments, such as described in paragraph [55], the temperature of second reaction scheme reaches 600 to 1000 deg C. with the residence time of the second reaction scheme being less than 0.1 sec.

[57] In some embodiments, such as any of those described in paragraphs [43]-[56], the condensable gases are greater than 1 wt % of the gaseous component and non-condensable gases are less than 99 wt % of the gaseous component, both on a dry basis.

[58] In some embodiments, such as described in paragraph [53], the condensable gases are greater than 5 wt % of the gaseous component and non-condensable gases are less than 95 wt % of the gaseous component, both on a dry basis.

[59] In some embodiments, such as described in paragraph [54], the condensable gases are at least 10 wt % of the gaseous component, and non-condensable gases are less than 90 wt % of the gaseous component, both on a dry basis.

[60] In some embodiments, such as any of those described in paragraphs [43]-[59], the first reaction scheme is terminated prior to equilibrium to obtain the composition of condensable gases that are hydrocarbons, and optionally, also the composition of the non-condensable gases that contain 2 or more carbon atoms.

[61] In some embodiments, such as any of those described in paragraphs [43]-[60], the second reaction scheme is performed in the presence of steam and the absence of molecular oxygen. In some embodiments, the amount of molecular oxygen in the feed to the second reaction scheme is not more than 1 wt %.

[62] In some embodiments, such as any of those described in paragraphs [43]-[61], at least 30 wt % of the olefins have carbon numbers between 2 and 4.

[63] In some embodiments, a process comprising:
converting a carbonaceous material with a first non-catalytic reaction scheme to reaction products comprising a gaseous component including gaseous olefins and a solid component including char; and converting at least a portion of the gaseous olefins with a second reaction scheme to hydrocarbons having a carbon number distribution of at least 5 carbon atoms.

[64] In some embodiments, such as described in paragraph [63], the reaction products of the first reaction scheme comprise more than 5% condensable gases on a dry basis.

[65] In some embodiments, such as described in paragraph [63] or [64], wherein condensable gases comprise hydrocarbons that are a liquid at 25 deg C. and 1 atm pressure.

[66] In some embodiments, such as any of those described in paragraphs [63]-[65], wherein the first reaction scheme comprises two reaction stages,
the first stage including conversion of the carbonaceous material at a lower temperature to condensable gases and the solid component,
the second stage comprising an operation comprising the conversion of at least a portion of the condensable gases and optionally a portion of the non-condensable gases that contain 2 or more carbon atoms at a higher temperature to the olefins.

[67] In some embodiments, such as any of those described in paragraphs [63]-[66], the hydrocarbons have a boiling range consistent with that of jet fuel.

[68] In some embodiments, such as any of those described in paragraphs [63]-[66], the hydrocarbons have a boiling range consistent with that of gasoline.

[69] In some embodiments, such as any of those described in paragraphs [63]-[66], the hydrocarbons have a boiling range consistent with that of diesel fuel.

[70] In some embodiments, such as any of those described in paragraphs [1]-[63], the non-condensable gases of the reaction products of the second reaction scheme, free of $CH_4$, CO, $CO_2$, COS, $H_2$, $H_2S$, $NH_3$, and $H_2O$, comprise at least 25 wt % olefins.

[71] In some embodiments, such as any of those described in paragraphs [1]-[63], the non-condensable gases of the reaction products of the second reaction scheme, free of $CH_4$, CO, $CO_2$, COS, $H_2$, $H_2S$, $NH_3$, and $H_2O$, comprise at least 35 wt % olefins.

[72] In some embodiments, such as any of those described in paragraphs [1]-[63], the non-condensable gases of the reaction products of the second reaction scheme, free of $CH_4$, CO, $CO_2$, COS, $H_2$, $H_2S$, $NH_3$, and $H_2O$, comprise at least 50 wt % olefins.

[73] In some embodiments, such as any of those described in paragraphs [1]-[63], the non-condensable gases of the reaction products of the second reaction scheme, free of $CH_4$, CO, $CO_2$, COS, $H_2$, $H_2S$, $NH_3$, and $H_2O$, comprise at least 60 wt % olefins.

[74] In some embodiments, such as those described in any of paragraphs [1]-[63], the non-condensable gases of the reaction products of the second reaction scheme, free of $CH_4$, CO, $CO_2$, COS, $H_2$, $H_2S$, $NH_3$, and $H_2O$, comprise at least 70 wt % olefins.

[75] In some embodiments, such as those described in any of paragraphs [70]-[74], the non-condensable gases of the reaction products of the second reaction scheme, free of $CH_4$, CO, $CO_2$, COS, $H_2$, $H_2S$, $NH_3$, and $H_2O$, comprise not more than 99.999 wt % olefins.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the claims should not be construed to limit the invention to the specific embodiments disclosed in the specification. Rather, the scope of the invention is to be determined entirely by the claims, which are to be construed in accordance with established doctrines of claim interpretation.

What is claimed is:

1. A process comprising:
converting a carbonaceous material with a first reaction scheme to a gaseous component comprising condensable gases and non-condensable gases and a solid component comprising char and ash, wherein a temperature of the first reaction scheme is in the range of 350 to 600 deg C.; and
converting at least a portion of the condensable gases and at least a portion of the non-condensable gases that contain 2 or more carbon atoms with a second reaction scheme to reaction products comprising olefins, wherein a temperature of the second reaction scheme is in the range of 600 to 1000 deg C. and a residence time of the second reaction scheme is less than 5 sec and at least 0.000001 sec; and wherein the portion of the condensable gases and the portion of the non-condensable gases that contain 2 or more carbon atoms are directly fed from the first reaction scheme to the second reaction scheme without being condensed;
wherein the second reaction scheme is steam cracking, and is performed in the absence of a catalyst, and in the presence of steam;
and wherein hydrogen is not added during the process.

2. The process of claim 1, wherein a residence time of the first reaction scheme is less than 5 sec, and at least 0.0001 sec.

3. The process of claim 1, wherein the carbonaceous material is solid.

4. The process of claim 1, wherein the first reaction scheme is pyrolysis performed in the absence of a catalyst.

5. The process of claim 1, further comprising separating the solid component from the gaseous component.

6. The process of claim 1, wherein the condensable gases are at least 5 wt % of the gaseous component on a dry basis, and not more than 99.9 wt %.

7. The process of claim 1, wherein non-condensable gases are not more than 95 wt % of the gaseous component on a dry basis, and not less than 0.000001 wt %.

8. The process of claim 1, wherein the second reaction scheme is performed in the absence of molecular oxygen.

9. The process of claim 1, wherein the condensable gases and the non-condensable gases that contain 2 or more carbon atoms that are converted in the second reaction scheme comprise at least 0.1 wt % oxygen on a dry basis, and not more than 95 wt %.

10. The process of claim 1, further comprising converting at least a portion of the reaction products from the second reaction scheme to a liquid product with a third reaction scheme wherein the liquid product is at least 60% by weight a liquid fuel.

11. The process of claim 10, wherein the third reaction scheme is performed in the presence of a catalyst.

12. The process of claim 11, wherein the third reaction scheme is oligomerization.

13. The process of claim 12, further comprising, prior to being fed to the third reaction scheme, cleaning the gaseous reaction products of the second reaction scheme to remove species that poison catalysts.

14. A process comprising:
converting a hydrocarbon material with a first non-catalytic reaction scheme to reaction products comprising a gaseous component comprising gaseous olefins and a solid component comprising char;
and
converting the gaseous olefins with a second reaction scheme to hydrocarbons having at least 5 carbon atoms;
wherein:
the first reaction scheme comprises two reaction stages, a first and a second stage;
the first stage comprising conversion of the carbonaceous material at a lower temperature to a product comprising a gas-phase component comprising condensable gases and the solid component, and
the second stage comprising conversion of at least a portion of the gas-phase component comprising the condensable gases at a higher temperature to the gaseous olefins;
wherein the portion of the gas-phase component is fed directly from the first stage to the second stage without condensing; and
wherein the second stage of the first reaction scheme is steam cracking, and is performed in the presence of steam;
wherein the reaction products of the second stage of the first reaction scheme comprise non-condensable gases, and the non-condensable gases, free of $CH_4$, CO, $CO_2$, COS, $H_2$, $H_2S$, $NH_3$, and $H_2O$, comprise at least 15 wt % olefins;
and wherein hydrogen is not added during the first reaction scheme.

15. The process of claim 14, wherein the reaction products of the first reaction scheme comprise more than 5 wt % condensable gases in the gaseous component on a dry basis.

16. The process of claim 14, wherein
the first stage of the first reaction scheme is at a temperature in the range of 350 to 600 deg C., and
the second stage of the first reaction scheme is at a temperature in the range of 600 to 1000 deg C.

17. The process of claim 1, wherein a residence time of the first reaction scheme is less than 1 sec, and at least 0.0001 sec.

18. The process of claim 1, wherein the residence time of the second reaction scheme is less than 1 sec.

19. The process of claim 1, wherein the residence time of the second reaction scheme is less than 0.1 sec.

20. The process of claim 1,
wherein the condensable gases and the non-condensable gases that contain 2 or more carbon atoms that are fed to the second reaction scheme comprise at least 1 wt % oxygen on a dry basis, and not more than 95 wt %.

21. The process of claim 1, wherein the reaction products of the second reaction scheme comprise gaseous hydrocarbons of an H:C ratio of 0.8 to 4.

22. The process of claim 1, wherein the reaction products of the second reaction scheme comprise gaseous hydrocarbons of an H:C ratio of 0.8 to 3.

23. The process of claim 12, wherein the feed to the third reaction scheme comprises oxygenated compounds.

24. The process of claim 14, wherein the non-condensable gases of the reaction products of the second stage of the first reaction scheme, free of $CH_4$, CO, $CO_2$, COS, $H_2$, $H_2S$, $NH_3$, and $H_2O$, comprise at least 25 wt % olefins.

25. The process of claim 1, wherein the temperature of the first reaction scheme is at a temperature in the range of 350 to 550 deg C.; and wherein the temperature of the second reaction scheme is at a temperature in the range of 600 to 620 deg C.

26. The process of claim 1, wherein the condensable gases and the non-condensable gases that contain 2 or more carbon atoms of the product of the first reaction scheme has an H:C ratio at least 5% higher than the H:C ratio of the carbonaceous material, and the portion of the products of the second reaction scheme comprising condensable gases and non-condensable gases that contain 2 or more carbon atoms has an O:C ratio at least 5% lower than the O:C ratio of the carbonaceous material.

27. The process of claim 26, wherein the condensable gases and the non-condensable gases that contain 2 or more carbon atoms of the product of the first reaction scheme has an H:C ratio at least 10% higher than the H:C ratio of the carbonaceous material, and the portion of the products of the second reaction scheme comprising condensable gases and non-condensable gases that contain 2 or more carbon atoms has an O:C ratio at least 10% lower than the O:C ratio of the carbonaceous material.

28. The process of claim 14, wherein the reaction products of the second stage of the first reaction scheme comprise non-condensable gases, and the non-condensable gases, free of $CH_4$, CO, $CO_2$, COS, $H_2$, $H_2S$, $NH_3$, and $H_2O$, comprise at least 35 wt % olefins.

29. The process of claim 12, wherein reaction products of the second reaction scheme are not subjected to any gas clean-up processes prior to being fed to the third reaction scheme.

30. The process of claim 1, wherein the O:C ratio (on a dry basis) of the combined products of the second reaction scheme is at least 5% lower than the O:C ratio of the carbonaceous material fed to the first reaction scheme.

31. The process of claim 1, wherein the O:C ratio (on a dry basis) of the products of the second reaction scheme exclusive of CO and $CO_2$ is not more than 95% of the O:C ratio of the carbonaceous material fed to first reaction scheme.

32. The process of claim 1, wherein the O:C ratio (on a dry basis) of the products of the second reaction scheme exclusive of CO and $CO_2$ is not more than 90% of the O:C ratio of the carbonaceous material fed to first reaction scheme.

33. The process of claim 1, wherein the O:C ratio (on a dry basis) of the products of the second reaction scheme exclusive of CO and $CO_2$ is not more than 80% of the O:C ratio of the carbonaceous material fed to first reaction scheme.

34. The process of claim 1, wherein the heat needed for the first reaction scheme is supplied by indirect heating.

35. The process of claim 1, wherein the gaseous component which is the product of the first reaction scheme is substantially free from molecular nitrogen.

36. The process of claim 1, wherein first reaction scheme and second reaction scheme are executed in two separate pieces of equipment.

37. The process of claim 1, wherein first reaction scheme and second reaction scheme are executed in one piece of equipment.

* * * * *